US012011251B2

(12) United States Patent
Lim et al.

(10) Patent No.: US 12,011,251 B2
(45) Date of Patent: Jun. 18, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Hye Rim Lim, Suwon-si (KR); Sang Yun Park, Hwaseong-si (KR); Jin Woo Choi, Suwon-si (KR); Jae Min Kang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 550 days.

(21) Appl. No.: 17/132,230

(22) Filed: Dec. 23, 2020

(65) Prior Publication Data
US 2022/0015650 A1 Jan. 20, 2022

(30) Foreign Application Priority Data
Jul. 15, 2020 (KR) .................. 10-2020-0087568

(51) Int. Cl.
A61B 5/021 (2006.01)
A61B 5/00 (2006.01)
A61B 5/02 (2006.01)
A61B 90/00 (2016.01)

(52) U.S. Cl.
CPC ........ *A61B 5/02116* (2013.01); *A61B 5/0033* (2013.01); *A61B 5/02007* (2013.01); *A61B 5/7475* (2013.01); *A61B 90/06* (2016.02); *A61B 2090/065* (2016.02)

(58) Field of Classification Search
None
See application file for complete search history.

(56) References Cited

U.S. PATENT DOCUMENTS

| 5,857,975 A | 1/1999 | Golub |
| 5,865,755 A | 2/1999 | Golub |
| 9,198,583 B2 | 12/2015 | Kim et al. |
| 10,238,312 B2 | 3/2019 | Eom et al. |
| 10,398,324 B2 | 9/2019 | Mukkamala et al. |
| 2010/0125212 A1 | 5/2010 | Kim et al. |
| 2015/0374249 A1 | 12/2015 | Elliott et al. |
| 2016/0089042 A1 | 3/2016 | Saponas et al. |

(Continued)

FOREIGN PATENT DOCUMENTS

| KR | 10-0609927 B1 | 8/2006 |
| KR | 10-2010-0055132 A | 5/2010 |

(Continued)

OTHER PUBLICATIONS

Communication dated Sep. 30, 2021, from the European Patent Office in European Application No. 21166258.0.

*Primary Examiner* — Michael R Bloch
(74) *Attorney, Agent, or Firm* — Sughrue Mion, PLLC

(57) ABSTRACT

An apparatus for estimating bio-information is provided. The apparatus for estimating bio-information may include a pulse wave sensor configured to measure a pulse wave signal from an object; a force sensor configured to measure a first force exerted between the object and the pulse wave sensor; and a processor configured to: convert the first force into a second force, based on structure information of the object; and estimate the bio-information, based on the pulse wave signal and the second force.

24 Claims, 20 Drawing Sheets

(56) References Cited

U.S. PATENT DOCUMENTS

| | | |
|---|---|---|
| 2019/0076032 A1 | 3/2019 | Park et al. |
| 2019/0175055 A1 | 6/2019 | Eom et al. |
| 2020/0037956 A1 | 2/2020 | Kang et al. |
| 2020/0093377 A1* | 3/2020 | Kwon ................. A61B 5/7278 |
| 2020/0359916 A1 | 11/2020 | Lee |

FOREIGN PATENT DOCUMENTS

| | | |
|---|---|---|
| KR | 10-2012-0007558 A | 1/2012 |
| KR | 10-2012-0057813 A | 6/2012 |
| KR | 10-2014-0148074 A | 12/2014 |
| KR | 10-2016-0055006 A | 5/2016 |
| KR | 10-1800705 B1 | 12/2017 |
| KR | 10-2018-0016885 A | 2/2018 |
| KR | 10-1892295 B1 | 8/2018 |
| KR | 10-1907675 B1 | 10/2018 |
| KR | 10-1918577 B1 | 2/2019 |
| KR | 10-2019-0030152 A | 3/2019 |
| KR | 10-2020-0014523 A | 2/2020 |
| WO | 2007/097702 A1 | 8/2007 |

\* cited by examiner

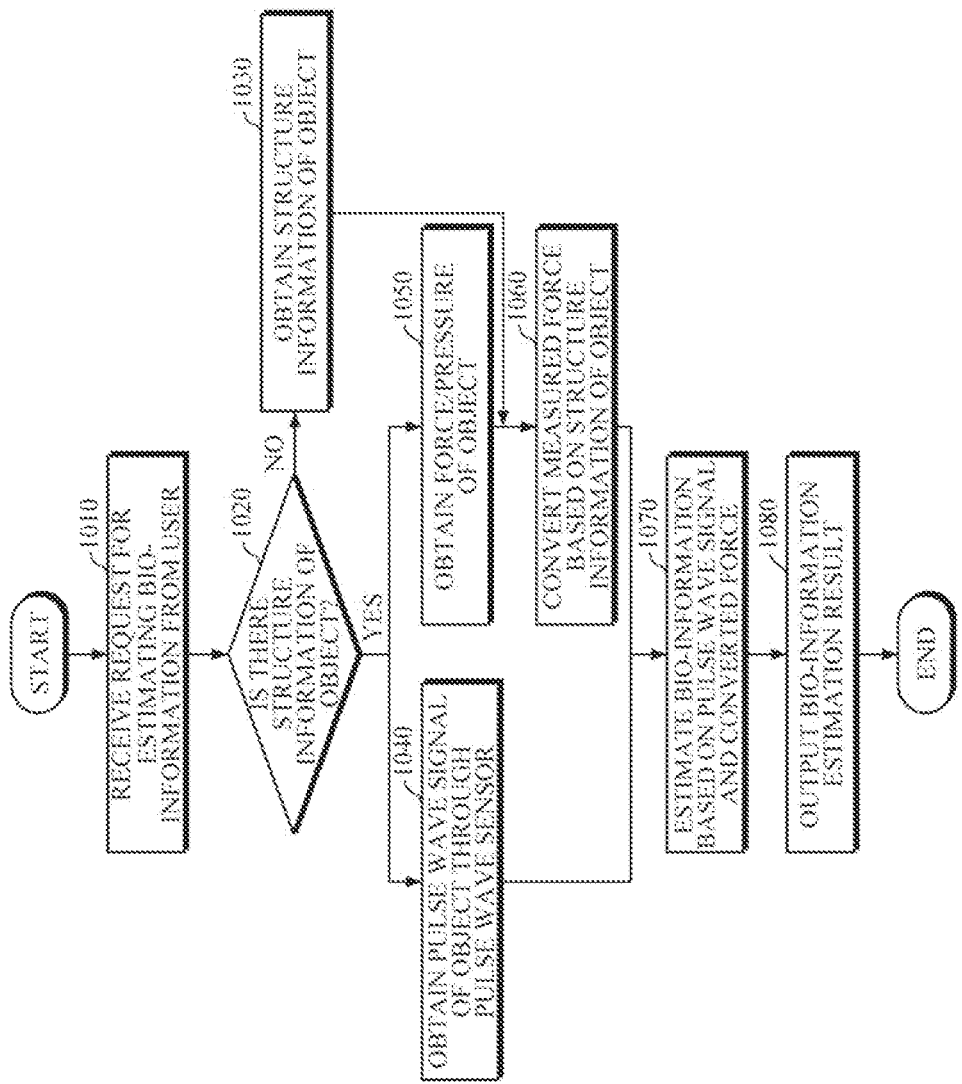

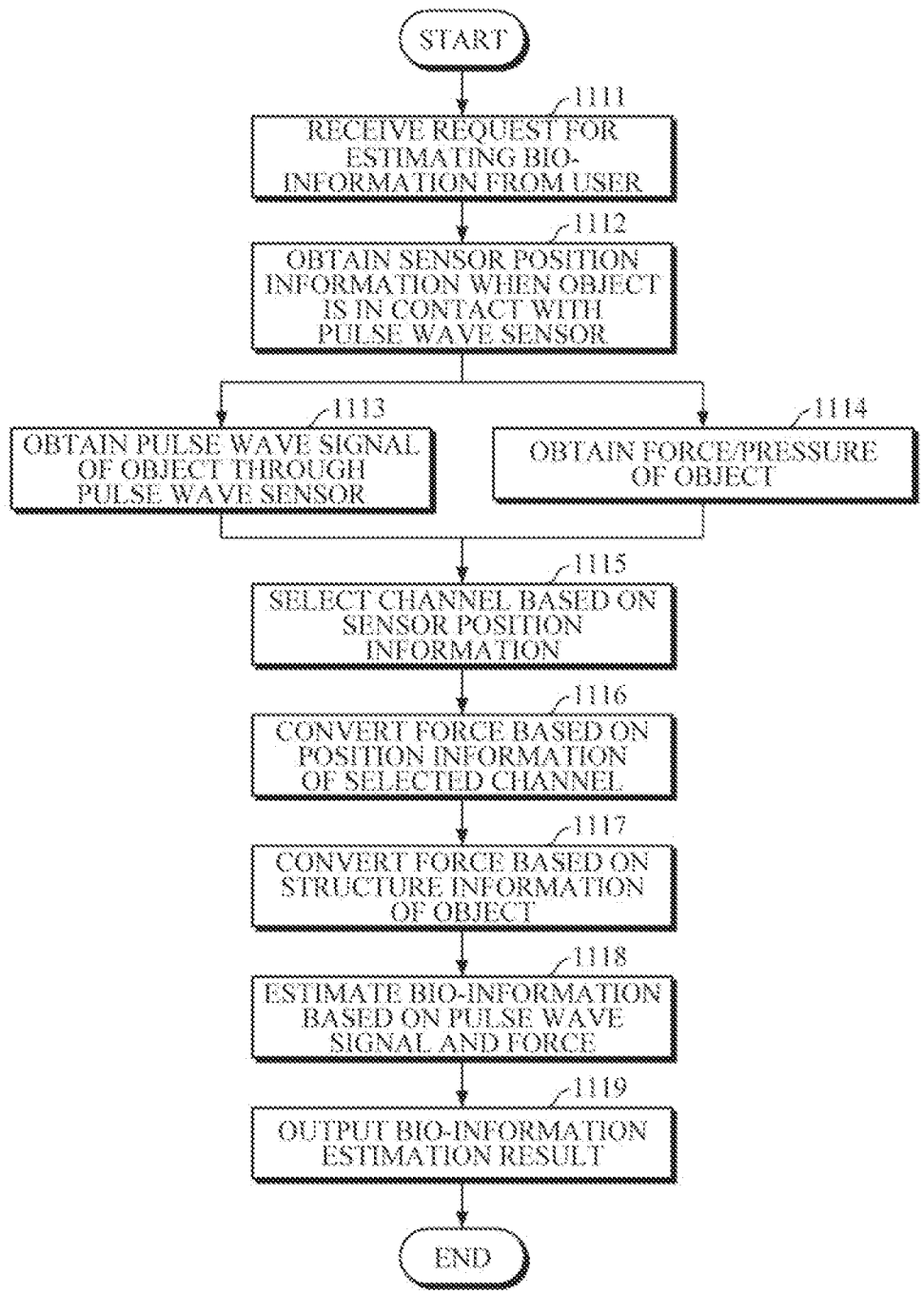

APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2020-0087568, filed on Jul. 15, 2020, in the Korean Intellectual Property Office, the disclosure of which is incorporated by reference herein in its entirety.

BACKGROUND

1. Field

The following description relates to an apparatus and method for estimating bio-information, and technology for cuffless blood pressure estimation.

2. Description of Related Art

General techniques for extracting cardiovascular characteristics, such as blood pressure, and the like, without using a pressure cuff include a pulse transit time (PTT) method and a pulse wave analysis (PWA) method.

The pulse transit time (PTT) method is a method of extracting cardiovascular characteristics by analyzing the shape of a photoplethysmography (PPG) signal or a body surface pressure signal obtained from a peripheral part of the body, e.g., a fingertip, a radial artery, or the like. The blood ejected from the left ventricle causes reflection at areas of large branches, such as the renal arteries and the iliac arteries, and the reflection affects the shape of the pulse wave or body pressure wave measured at the peripheral part of the body. Thus, by analyzing this shape, arterial stiffness, arterial age, aortic artery pressure waveform of the like can be inferred.

The PWV method is a method of extracting cardiovascular characteristics, such as arterial stiffness, blood pressure, or the like, by measuring a pulse wave transmission time. In this method, a delay (a pulse transit time (PTT)) between an R-peak (left ventricular contraction interval) of an electrocardiogram (ECG) and a peak of a PPG signal of a finger or the radial artery is measured by measuring the ECG and PPG signals of the peripheral part of the body and by calculating a velocity at which the blood from the heart reaches the peripheral part of the body by dividing an approximate length of the arm by the PTT.

SUMMARY

Additional aspects will be set forth in part in the description which follows and, in part, will be apparent from the description, or may be learned by practice of the presented embodiments.

According to an aspect of an example embodiment, an apparatus for estimating bio-information may include a pulse wave sensor configured to measure a pulse wave signal from an object; a force sensor configured to measure a first force exerted between the object and the pulse wave sensor; and a processor configured to: convert the first force into a second force, based on structure information of the object; and estimate the bio-information, based on the pulse wave signal and the second force.

The structure information of the object comprises at least one of a blood vessel position, a blood vessel depth, and a bone depth.

The processor is further configured to obtain the structure information of the object based on a user input and at least one of an optical image, an ultrasonic image, a magnetic resonance imaging (MRI) image, and a photoacoustic image of the object.

The processor is further configured to convert the first force into the second force, based on at least one of a ratio between the blood vessel depth and the bone depth and a difference between the blood vessel depth and the bone depth.

The processor is further configured to obtain sensor position information of the pulse wave sensor with respect to the object, based on the object being in contact with the pulse wave sensor.

The processor is further configured to obtain the sensor position information by analyzing a relative position between the object and the pulse wave sensor, based on an image of the object being in contact with the pulse wave sensor.

The apparatus further comprises a fingerprint sensor, and wherein the processor is further configured to obtain the sensor position information, based on a fingerprint image obtained by the fingerprint sensor.

The processor is further configured to convert the first force into a third force, based on the sensor position information, and convert the third force into the second force in which the structure of the object is reflected.

The processor is further configured to convert the first force into the third force, based on a distance between a predetermined reference point of the object and the sensor position.

By using a pre-defined function, the processor is further configured to obtain a first correction value, based on the distance between the reference point and the sensor position; obtain a second correction value, based on a distance between the reference point and a reference position; and convert the first force into the third force, based on the first correction value and the second correction value.

The pulse wave sensor has a plurality of channels for measuring pulse wave signals at a plurality of points of the object, and the processor is further configured to select at least one of the plurality of channels, based on a blood vessel position of the object and the sensor position; and convert the first force into the third force, based on a distance between the predetermined reference point of the object and the selected channel.

The processor is further configured to select a channel, which is located closest to the blood vessel position of the object, based on the sensor position information.

The apparatus further comprises an area sensor configured to measure a contact area between the object and the pulse wave sensor, based on the object being in contact with the pulse wave sensor and changing a force applied to the pulse wave sensor.

The processor is further configured to obtain a contact pressure, based on the second force and the measured contact area; and estimate the bio-information, based on the contact pressure and the pulse wave signal.

The bio-information comprises one or more of blood pressure, vascular age, arterial stiffness, aortic pressure waveform, vascular compliance, stress index, fatigue level, skin age, and skin elasticity.

According to an aspect of an example embodiment, a method of estimating bio-information may include measuring a pulse wave signal from an object; measuring a first force exerted between the object and a pulse wave sensor; converting the first force into a second force, based on structure information of the object; and estimating the bio-information based on the pulse wave signal and the second force.

The structure information of the object comprises at least one of a blood vessel position, a blood vessel depth, and a bone depth.

In response to receiving a request for estimating the bio-information from a user, the method includes determining whether the structure information of the object of the user exists; and in response to determining that the structure information of the object does not exist, obtaining the structure information of the object.

The converting of the first force comprises converting the first force, based on at least one of a ratio and a difference between the blood vessel depth and the bone depth.

The method further comprises obtaining sensor position information of a pulse wave sensor with respect to the object when the object is in contact with the pulse wave sensor.

The converting of the first force into the second force comprises converting the first force into a third force, based on the sensor position information; and converting the third force into the second force, based on the structure information of the object.

The converting of the first force into the third force comprises converting the first force into the third force, based on a distance between a predetermined reference point of the object and the sensor position.

The converting of the first force into the third force comprises, by using a pre-defined function, obtaining a first correction value based on the distance between the reference point and the sensor position; obtaining a second correction value based on a distance between the reference point and a reference position; and converting the first force into the third force, based on the first correction value and the second correction value.

The converting of the first force into the third force comprises, in response to the pulse wave sensor having a plurality of channels for measuring pulse wave signals at a plurality of points of the object, selecting at least one of the plurality of channels based on blood vessel position information of the object and the sensor position information; and converting the first force into the third force, based on a distance between a predetermined reference point of the object and the at least one of the plurality of channels.

The method further comprises measuring a contact area, based on the object being in contact with the pulse wave sensor and changing a force applied to the pulse wave sensor.

The estimating of the bio-information comprises obtaining a contact pressure, based on the second force and the contact area; and estimating the bio-information, based on the contact pressure and the pulse wave signal.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 10 is a flowchart illustrating a method of estimating bio-information according to an embodiment of the present disclosure;

FIG. 11 is a flowchart illustrating a method of estimating bio-information according to another embodiment of the present disclosure;

DETAILED DESCRIPTION

Figure 1A:
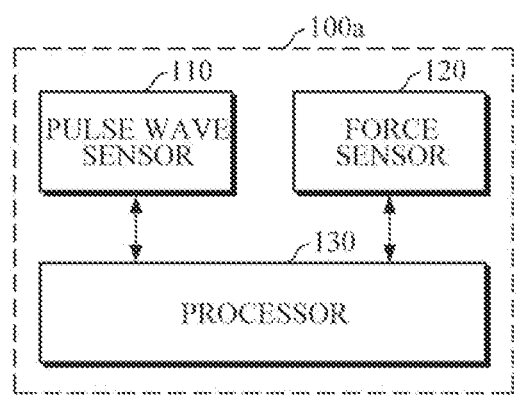
FIGS. 1A and 1B are block diagrams illustrating an apparatus for estimating bio-information according to embodiments of the present disclosure.

Details of example embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms "first," "second," etc. may be used herein to describe various elements, these elements should not be limited by these terms. These terms are only used to distinguish one element from another. Also, the singular forms of terms are intended to include the plural forms of the terms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Hereinafter, embodiments of an apparatus and method for estimating bio-information will be described in detail with reference to the accompanying drawings.

Figure 1B:
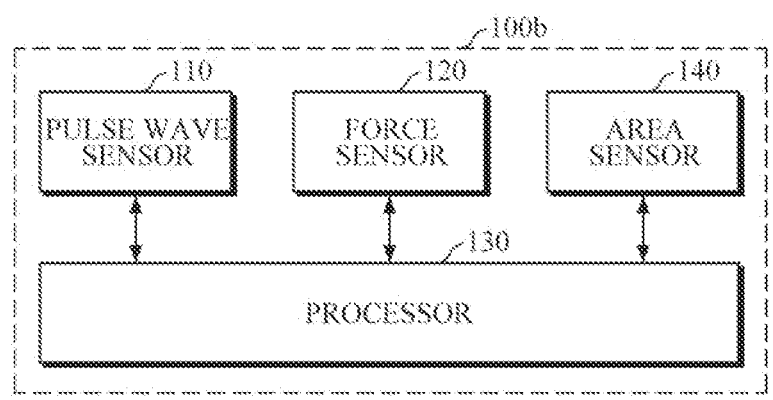

FIGS. 1A and 1B are block diagrams illustrating an apparatus for estimating bio-information according to embodiments of the present disclosure.

The apparatuses 100a and 100b for estimating bio-information according to embodiments of the present disclosure may be mounted in terminals, such as a smart phone, a tablet personal computer (PC), a desktop component, a laptop computer, etc., wearable devices, and the like. In this case, examples of the wearable devices may include a wristwatch-type wearable device, a bracelet-type wearable device, a wristband-type wearable device, a ring-type wearable device, a glasses-type wearable device, a headband-type wearable device, etc., but the wearable devices are not limited thereto.

Referring to FIG. 1A, the apparatus 100a for estimating bio-information according to an embodiment includes a pulse wave sensor 110, a force sensor 120, and a processor 130. Furthermore, referring to FIG. 1B, the apparatus 100b for estimating bio-information according to another embodiment further includes an area sensor 140 in addition to the pulse wave sensor 110, the force sensor 120, and the processor 130.

The pulse wave sensor 110 measures a photoplethysmography (PPG) signal (hereinafter referred to as a "pulse wave signal") from an object. In this case, the object may be a body area which may come into contact with the pulse wave sensor 110, and may be a body part at which pulse waves may be easily measured by PPG. For example, the object may be a finger where blood vessels are densely located, but the object is not limited thereto and may be an area on the wrist that is adjacent to the radial artery, or a peripheral part of the body, such as an upper portion of the wrist, toes, etc., where veins or capillaries are located.

The pulse wave sensor 110 may include one or more light sources for emitting light onto the object, and one or more light receivers which are disposed at a predetermined distance from the light sources and detect light scattered or reflected from the object. The light sources may emit light of different wavelengths. For example, the light sources may emit light of an infrared wavelength, a green wavelength, a blue wavelength, a red wavelength, a white wavelength, and the like. The light sources may include a light emitting diode (LED), a laser diode (LD), a phosphor, etc., but are not limited thereto. Further, the light receivers may include a photodiode, a photodiode array, a complementary metal-oxide semiconductor (CMOS) image sensor, a charge-coupled device (CCD) image sensor, and the like.

The pulse wave sensor 110 may have a single channel including a light source and a light receiver, so as to measure a pulse wave signal at a specific point of the object. Alternatively, the pulse wave sensor 110 may have multiple channels to measure a plurality of pulse wave signals at multiple points of the object. Each of the channels of the pulse wave sensor 110 may be formed in a pre-defined shape such as a circular shape, an oval shape, a fan shape, etc., so that pulse wave signals may be measured at multiple points of the object. Each channel of the pulse wave sensor 110 may include one or more light sources and one or more light receivers. Further, each channel may include two or more light sources to emit light of a plurality of wavelengths. Alternatively, the pulse wave sensor 110 may be configured to measure a plurality of pulse wave signals in a predetermined area of the object. For example, the pulse wave sensor 110 may include one or more light sources, and a light receiver formed as a CMOS image sensor and disposed at a predetermined distance from the one or more light sources.

When a user places an object on the pulse wave sensor 110 and increases or decreases a pressing force to induce a change in pulse wave amplitude, the force sensor 120 may measure a contact force exerted between the pulse wave sensor 110 and the object. The force sensor 120 may include a strain gauge, and the like.

The area sensor 140 may obtain a contact area when the object is in contact with the pulse wave sensor 110 and changes pressure. The area sensor 140 may be disposed at an upper end or a lower end of the pulse wave sensor 110.

However, the apparatuses 100a and 100b for estimating bio-information are not limited thereto, and may include a pressure sensor for measuring pressure between the object and the pulse wave sensor 110 and the like, instead of including the force sensor 120 and the area sensor 140.

The processor 130 may estimate bio-information based on the pulse wave signal obtained by the pulse wave sensor 110, the contact force obtained by the force sensor 120, and/or the contact area obtained by the area sensor 140. In this case, the bio-information may include blood pressure, vascular age, arterial stiffness, aortic pressure waveform, vascular compliance, skin elasticity, skin age, stress index, fatigue level, etc., but is not limited thereto.

For example, in order to improve accuracy in estimating bio-information, the processor 130 may estimate bio-information by considering anatomical structure information of the object. For example, the processor 130 may convert the contact force, measured by the force sensor 120, into a force in which structure information is reflected, and may estimate bio-information based on the pulse wave signal, the converted force, and/or the contact area.

Figure 2:
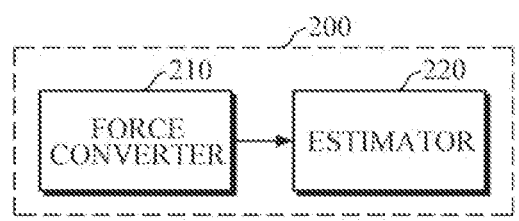
FIG. 2 is a diagram illustrating an example of a configuration of a processor of FIGS. 1A and 1B.
Figure 3A:
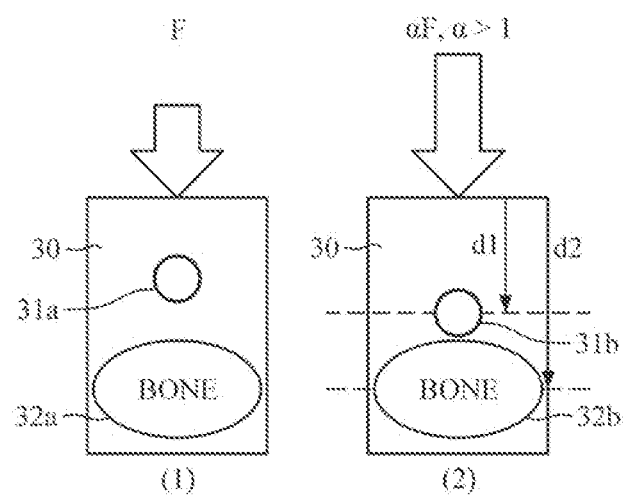
FIGS. 3A and 3B are diagrams explaining a relationship between an anatomical structure of an object and a force.
Figure 3B:
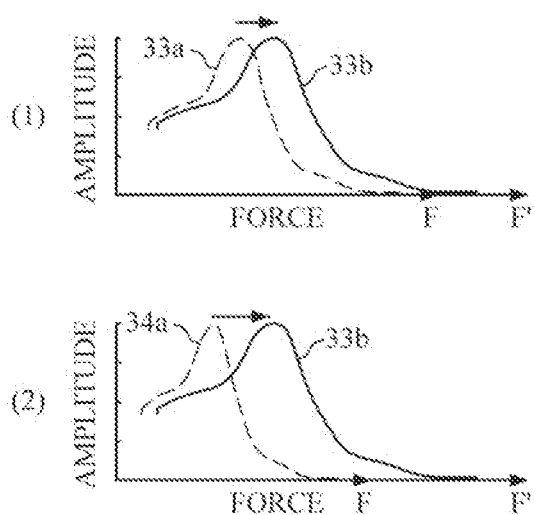
Figure 4A:
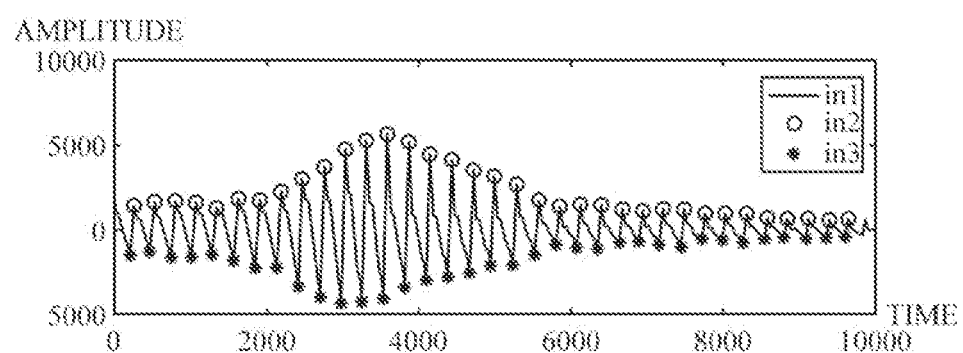
FIGS. 4A and 4B are diagrams explaining an example of estimating blood pressure using oscillometry.
Figure 4B:
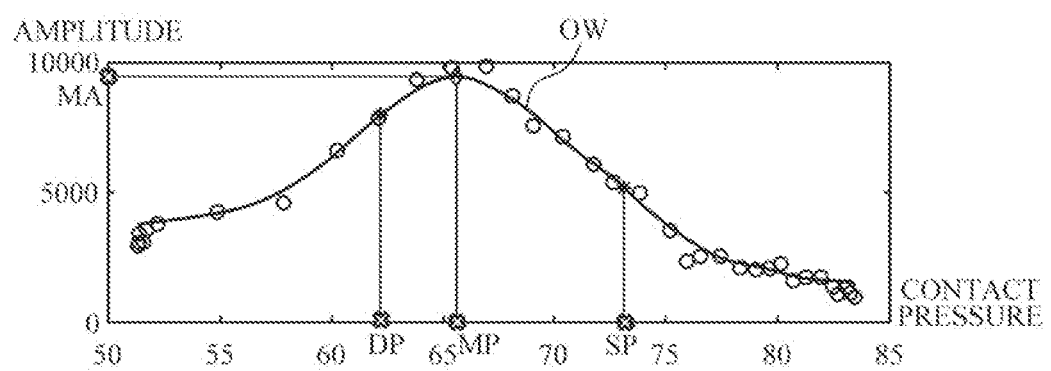

FIG. 2 is a diagram illustrating an example of a configuration of the processor 130 of FIGS. 1A and 1B. FIGS. 3A and 3B are diagrams explaining a relationship between an anatomical structure of an object and a force. FIGS. 4A and 4B are diagrams explaining an example of estimating blood pressure using oscillometry.

Referring to FIG. 2, a processor 200 includes a force converter 210 and an estimator 220.

Generally, when pressure is applied at a position away from the position of a finger artery, the force applied to the actual artery may be lost due to a finger's soft tissue. That is, there may be a difference between a force measured by a force sensor and a force actually applied to the artery, thereby causing an error in estimation of contact pressure of the finger and reducing accuracy in estimating blood pressure.

The force converter 210 may convert the measured contact force or contact pressure into a contact force or contact pressure in which anatomical structure information of the object is reflected. In this case, the anatomical structure information of the object may include a blood vessel position, a blood vessel depth, a bone depth, etc., but is not limited thereto. The force converter 210 may convert the contact force into contact pressure by using a pre-defined conversion model, the contact area obtained by the area sensor 140, an area of the pulse wave sensor 110, and the like.

For convenience of explanation, the following description will be given of an example of converting a contact force, but the example may also include converting a contact force into contact pressure and then converting the contact pressure.

FIG. 3A is a diagram explaining an example of converting a force based on an anatomical structure of an object 30. For example, assuming that bones 32a and 32b are located at the same depth, (1) illustrates a case where a blood vessel 31a is positioned relatively far away from the bone 32a in the object 30, i.e., a case where the blood vessel 31a is located at a shallow depth from the surface of the object 30; compared to the case of (1), (2) illustrates a case where a blood vessel 31b is positioned close to the bone 32b, i.e., a case where the blood vessel 31b is located at a relatively deep depth from the surface of the object 30. In the case of (2), the blood vessel 31b is positioned relatively close to the bone 32b compared to the case of (1), such that an actual force applied to the blood vessel 31b is less than an external force applied to the object 30. Accordingly, assuming that in the case of (1), mean arterial pressure (MAP) is applied to the blood vessel 31a when a force F is applied, in the case of (2) it is required to apply a force αF, which is relatively greater than the force F, to apply equal MAP to the blood vessel 31b.

By using a conversion equation, such as the following Equation 1 which is defined based on the above relationship, the force converter 210 may convert the force, measured by the force sensor 120, into a force in which structure information of the object is reflected.

$$F' = F\frac{d2}{d1} \qquad \text{[Equation 1]}$$

Herein, F denotes the contact force measured by the force sensor 120; F' denotes a force converted by reflecting the structure information of the object; d1 denotes a depth of the blood vessel from the surface of the object; and d2 denotes a depth of the bone from the surface of the object.

The conversion equation such as the above Equation 1 shows an example of conversion by applying a ratio between the depth of the blood vessel and the depth of the bone, but is not limited thereto, and may be defined as a conversion equation of various combinations such as a difference between the depth of the blood vessel and the depth of the bone (e.g., d2-d1), and the like. In this case, a weight may be applied to each of the depth of the blood vessel and/or the depth of the bone according to individual characteristics such as user characteristics or object characteristics, and the weighted depth of the blood vessel and/or the weighted depth of the bone may be combined.

Once the force converter 210 converts the measured force into the force in which the anatomical characteristics of the object are reflected, the estimator 220 may estimate bio-information based on oscillometry using the converted force and the pulse wave signal.

In FIG. 3B, (1) illustrates a change from an oscillogram 33a of force F before conversion to an oscillogram 33b of force F' after conversion in the case where the blood vessel is located at a relatively shallow depth as illustrated in (1) of FIG. 3A; and (2) illustrates a change from an oscillogram 34a of force F before conversion to an oscillogram 34b of force F' after conversion in the case where the blood vessel is located at a relatively deep depth as illustrated in (2) of FIG. 3A. In the case of (2) where the blood vessel is located at a relatively deep depth, a shift width of the oscillogram is relatively greater when compared to the case of (1) where the blood vessel is located at a shallow depth.

FIGS. 4A and 4B are diagrams explaining an example of estimating blood pressure using oscillometry.

Referring to FIGS. 4A and 4B, the estimator 220 may extract, e.g., a peak-to-peak point of the pulse wave signal waveform by subtracting a negative (−) amplitude value in3 from a positive (+) amplitude value in2 of a waveform envelope in1 at each measurement time of the pulse wave signal, and may obtain an oscillogram (OW) by plotting the peak-to-peak amplitude at each measurement time against the contact pressure value at a corresponding time and by performing, for example, polynomial curve fitting.

Further, the estimator 220 may extract characteristic points for estimating blood pressure from the generated oscillogram OW, and may estimate blood pressure by using the extracted characteristic points. For example, the estimator 220 may extract, as characteristic points, a contact pressure value MP at a maximum point of the pulse wave, contact pressure values DP and SP at points corresponding to amplitude values having a preset ratio (e.g., 0.5 to 0.7) to a maximum amplitude value MA, and the like from the oscillogram OW. The estimator 220 may determine, for example, the contact pressure value MP itself as MAP, and may determine the contact pressure value DP as DBP and the contact pressure value SP as SBP. Alternatively, by applying each of the extracted contact pressure values MP, DP, and SP to a pre-defined blood pressure estimation model, the estimator 220 may estimate MAP, DBP, and SBP independently. In this case, the blood pressure estimation model may be expressed in the form of various linear or non-linear combination functions, such as addition, subtraction, division, multiplication, logarithmic value, regression equation, and the like, with no particular limitation.

Figure 5:
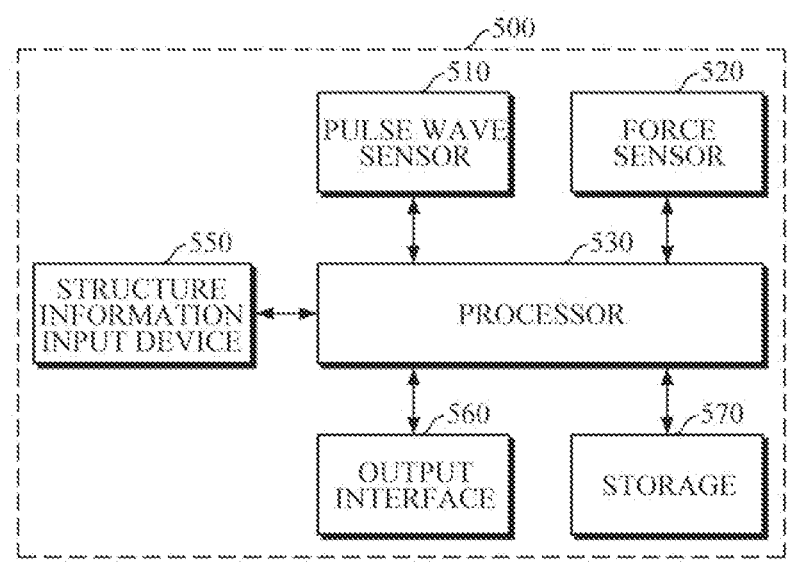
FIG. 5 is a block diagram illustrating an apparatus for estimating bio-information according to another embodiment of the present disclosure.
Figure 6A:
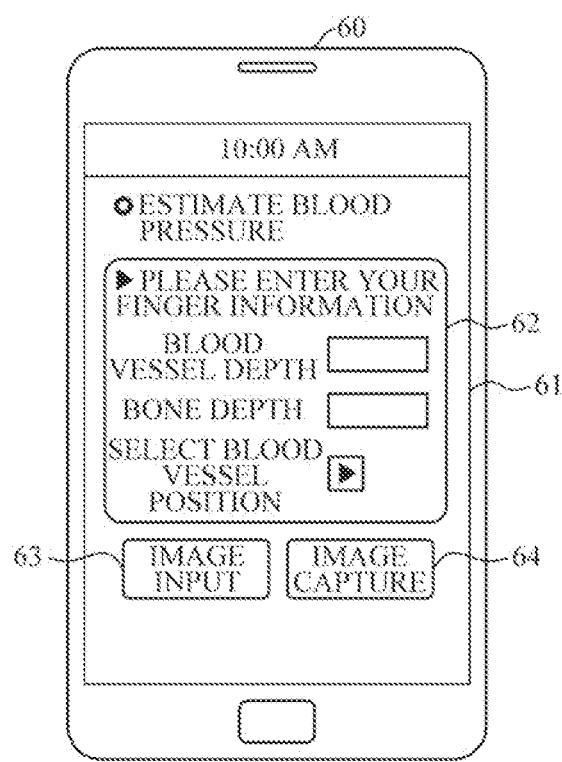
FIGS. 6A to 6C are diagrams explaining an example of obtaining structure information of an object.
Figure 6B:
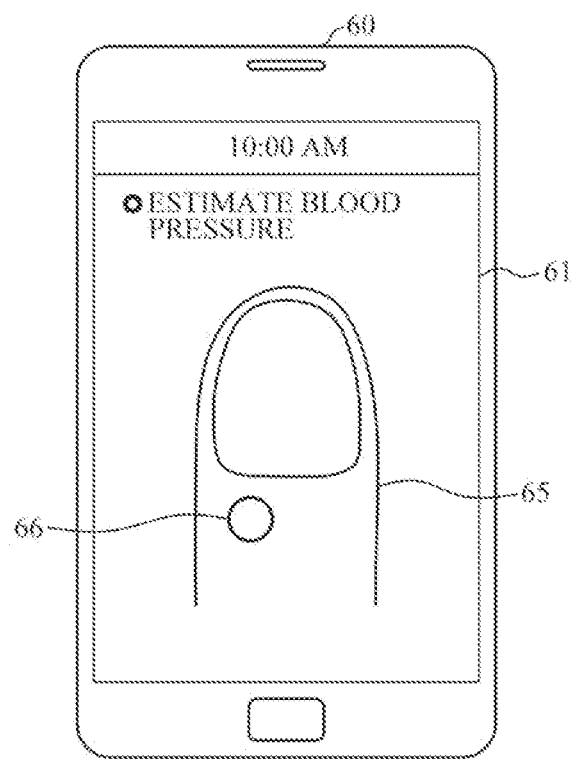
Figure 6C:
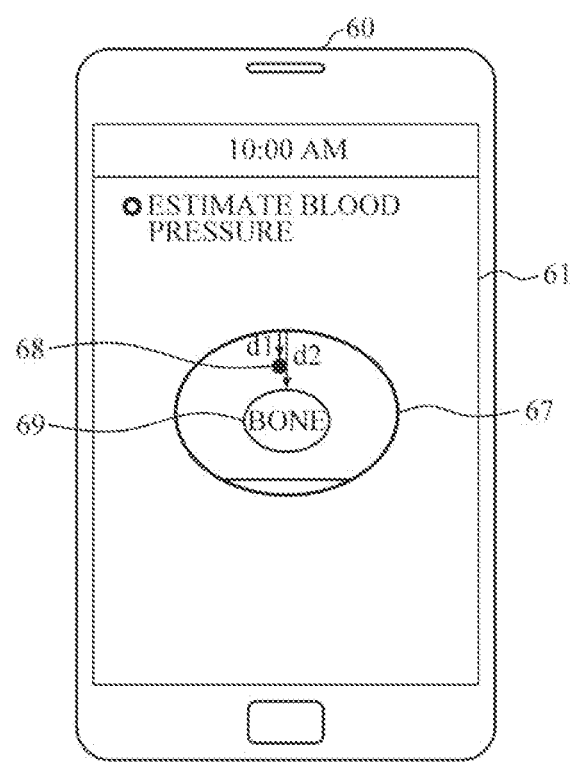

FIG. 5 is a block diagram illustrating an apparatus for estimating bio-information according to another embodiment of the present disclosure. FIGS. 6A to 6C are diagrams explaining an example of obtaining structure information of an object.

Referring to FIG. 5, the apparatus 500 for estimating bio-information includes a pulse wave sensor 510, a force sensor 520, a processor 530, a structure information input device 550, an output interface 560, and a storage 570. The pulse wave sensor 510, the force sensor 520, and the processor 530 are described above in detail with reference to FIGS. 1A to 2. In the embodiment of FIG. 5, the apparatus 500 for estimating bio-information may further include the area sensor of FIG. 1B.

The structure information input device 550 may obtain structure information of an object at a time when a user is registered. Further, in response to a user's request for estimating bio-information, the structure information input device 550 may check whether there is structure information of the object of the user in the storage 570 or whether it is time to calibrate the information; and if there is no structure information of the object or if it is time to calibrate the information, the structure information input device 550 may obtain structure information of the object from the user. At least some function of the structure information input device 550 may be integrated with the processor 530.

The structure information input device 550 may directly receive input of the structure information of an object from a user, or may obtain the structure information of the object by using an optical image, an ultrasonic image, a magnetic resonance imaging (MRI) image, a photoacoustic image, etc., of the object. The following examples of obtaining structure information of the object are merely exemplary, and the present disclosure is not limited thereto.

For example, FIG. 6A illustrates a smart device 60, to which the apparatus 500 for estimating bio-information according to the embodiment is applied, in which the structure information input device 550 may output an interface 62 on a display 61 through the output interface 560 so that the user may directly input structure information of the object through the interface 62. As illustrated in FIG. 6A, the interface 62 may display a graphic object for the user to enter a blood vessel depth and a bone depth. Further, a graphic object in the form of a button may be displayed for the user to directly designate a blood vessel position.

When the user clicks the button to directly designate the blood vessel position in FIG. 6A, the structure information input device 550 may display a finger image 65 on the display 61, as illustrated in FIG. 6B. The user may directly designate a blood vessel position 66 on the finger image 65 by using an input means (e.g., finger, touch pen, etc.); and once the user designates the blood vessel position 66, the structure information input device 550 may display a marker, indicating the blood vessel position of the object, on the finger image 65.

In another example, as illustrated in FIG. 6A, the structure information input device 550 may display a graphic object 63 in the form of a button on the display 61, so as to receive an object image captured by an external image capturing device. In this case, the object image may be an optical image, an ultrasonic image, a magnetic resonance imaging (MRI) image, a photoacoustic image, etc., which are captured by an external image capturing device, but the image is not limited thereto.

Once the user clicks the graphic object 63, the structure information input device 550 checks whether there is an image of a structure of the object which is pre-stored in the storage 570; and if there is no image, the structure information input device 550 may receive an image from an external image capturing device through a communication module mounted in the smartphone 60 and may store the received image in the storage 570. In this case, the communication module may communicate with the external device by using various wireless or wired communication techniques, such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, mobile communication, and the like. However, this is merely exemplary and is not intended to be limiting.

The structure information input device 550 may analyze the captured image of the object structure, may store an analysis result in the storage 570, and may visually display the analysis result on the display 610 as illustrated in FIG. 6C. For example, as illustrated in FIG. 6C, the structure information input device 550 may display a finger image 67 and may display markers 68 and 69, indicating positions of the blood vessel and bone, on the finger image 67. Further, the structure information input device 550 may visually display a depth d1 of the blood vessel and a depth d2 of the bone.

In another example, as illustrated in FIG. 6A, the structure information input device 550 may display a graphic object 64 in the form of a button on the display 61 so that a user may directly capture a finger image. In the case where a smartphone 60 has, for example, an ultrasonic sensor, the structure information input device 550 may control the ultrasonic sensor to acquire an ultrasonic image of a user's finger. Alternatively, if the smartphone 60 has no device for capturing a finger image, the structure information input device 550 may be connected to an external image capturing device through the communication module, and once the external image capturing device acquires a finger image, the structure information input device 550 may receive the acquired image from the external device. The structure information input device 550 may obtain finger structure information by analyzing the received image, and may store the obtained finger structure information in the storage 570.

The output interface 560 may output the pulse wave signal measured by the pulse wave sensor 510, the contact force measured by the force sensor 520, the contact area obtained by the area sensor, the contact pressure, and/or a processing result of the processor 530. The output interface 560 may provide a user with the information by various visual/non-visual methods using a display, a speaker, a haptic device, and the like. For example, the output interface 560 may output the measured pulse wave signal in the form of graphs. Further, the output interface 560 may visually display an estimated bio-information value of a user by using various visual methods, such as by changing color, line thickness, font, and the like, based on whether the estimated blood pressure value falls within or outside a normal range. Alternatively, upon comparing the estimated bio-information value with a previous estimation history, if it is determined that the estimated bio-information value is abnormal, the output interface 560 may provide a warning message and the like, as well as guide information on a user's action such as food information that the user should be careful about, related hospital information, and the like.

The storage 570 may store a variety of information for estimating bio-information. For example, the storage 570 may store the pulse wave signal measured by the pulse wave sensor 510, the contact force measured by the force sensor 520, the contact area obtained by the area sensor, a processing result of the object, a bio-information estimation model, a captured image of an object structure, and the like. Further, the storage 570 may store each user's characteristics information such as a user's age, gender, health condition, object structure information, and the like. However, the information is not limited thereto.

The storage 570 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 7:
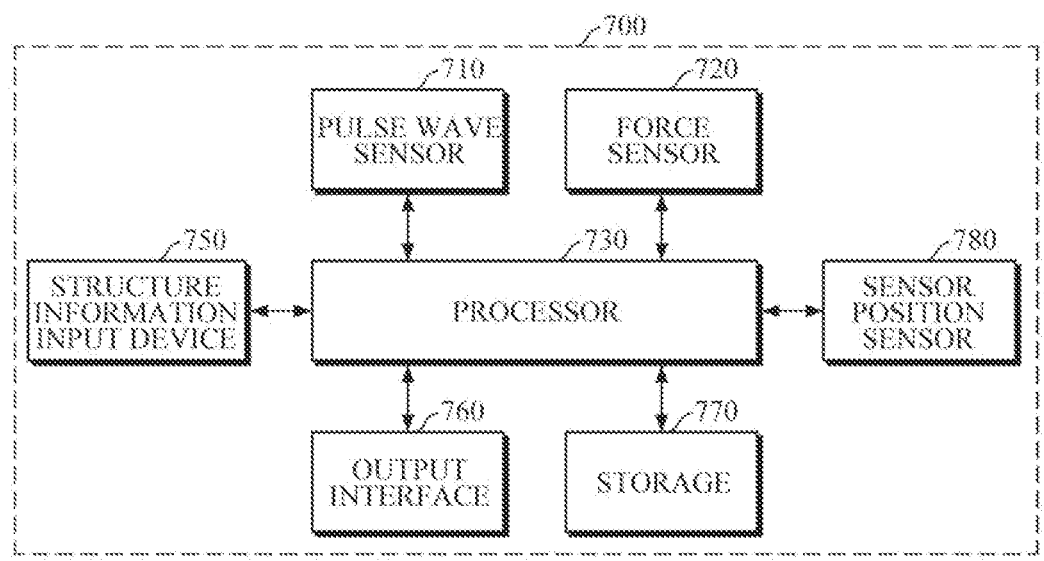
FIG. 7 is a block diagram illustrating an apparatus for estimating bio-information according to yet another embodiment of the present disclosure.
Figure 8:
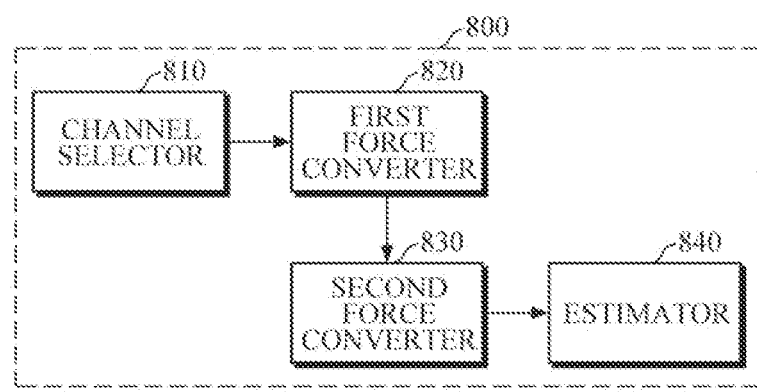
FIG. 8 is a diagram illustrating an example of a configuration of a processor of FIG. 7.
Figure 9A:
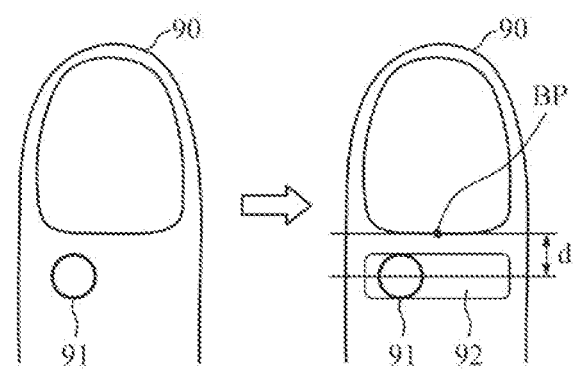
FIGS. 9A to 9C are diagrams explaining examples of estimating blood pressure by using sensor position information of an object.
Figure 9B:
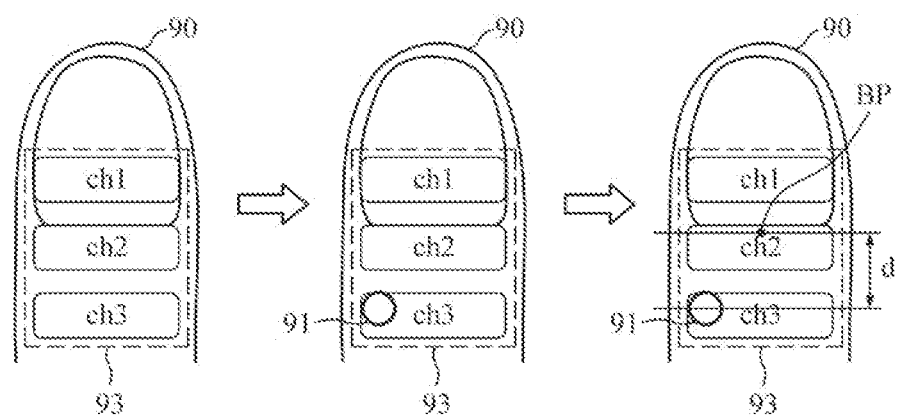
Figure 9C:
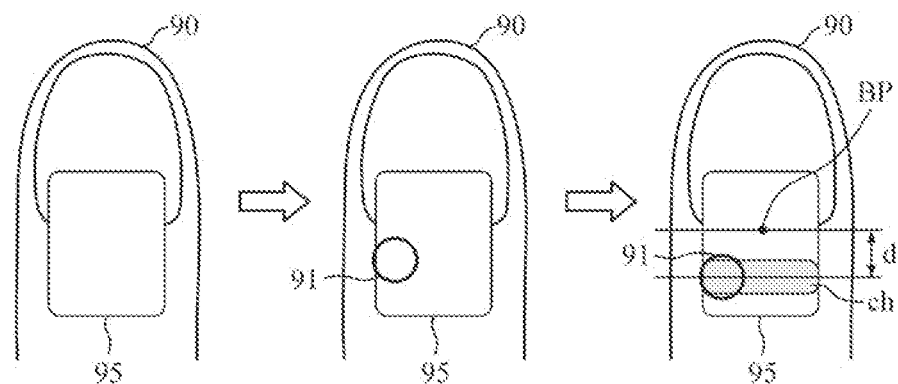

FIG. 7 is a block diagram illustrating an apparatus for estimating bio-information according to yet another embodiment of the present disclosure. FIG. 8 is a diagram illustrating an example of a configuration of a processor of FIG. 7. FIGS. 9A to 9C are diagrams explaining examples of estimating blood pressure by using sensor position information of an object.

Referring to FIG. 7, the apparatus 700 for estimating bio-information according to an embodiment includes a pulse wave sensor 710, a force sensor 720, a processor 730, a structure information obtainer 750, an output interface 760, a storage 770, and a sensor position sensor 780. The pulse wave sensor 710, the force sensor 720, the processor 730, the structure information obtainer 750, the output interface 760, and the storage 770 are described above in detail with reference to FIGS. 1A to 6C. In this embodiment, the apparatus 700 for estimating bio-information may further include the area sensor of FIG. 1B.

When an object is in contact with the pulse wave sensor 710, the sensor position sensor 780 may obtain sensor position information of the pulse wave sensor 710 on the object when the object is in contact with the pulse wave sensor 710. At least some function of the sensor position sensor 780 may be integrated with the processor 730.

For example, the sensor position sensor 780 may obtain the sensor position information based on object images captured by an external image capturing device. The external image capturing device may be a camera module installed at a fixed location or a camera module mounted in a mobile device such as a smartphone and the like. For example, once the external image capturing device captures an image of the finger being in contact with the pulse wave sensor 710, the sensor position sensor 780 may receive the image of the finger through a communication module mounted in the apparatus 700 for estimating bio-information.

By analyzing a relative position between the pulse wave sensor 710 and the finger based on the image of the finger, the sensor position sensor 780 may obtain the position of the finger, being in contact with the pulse wave sensor 710, as a sensor position. Further, if the external image capturing device, having the function of obtaining a sensor position, obtains sensor position information by capturing an image of the finger, the sensor position sensor 780 may receive the sensor position information from the external image capturing device through the communication module.

In another example, the sensor position sensor 780 may include a fingerprint sensor for obtaining a fingerprint image of the object being in contact with the pulse wave sensor 710. The fingerprint sensor may be disposed at an upper end or a lower end of the pulse wave sensor 710. The sensor position sensor 780 may estimate a sensor position by analyzing a change in fingerprint pattern based on the fingerprint image of the object. For example, when a finger applies pressure to the pulse wave sensor 710, a contact position between the finger and the pulse wave sensor 710 is pressed more than other positions of the finger, such that a distance between ridges or valleys of a fingerprint at the contact position between the finger and the pulse wave sensor 710 is larger than other positions. If a distance between ridges or valleys of the fingerprint at a predetermined position of the finger is greater than or equal to a predetermined threshold value when compared to other positions, the sensor position sensor 780 may obtain the position as a sensor position.

Once the sensor position sensor 780 obtains the sensor position, the processor 730 may estimate bio-information based on the sensor position and a blood vessel position.

Referring to FIG. 8, the processor 800 according to an embodiment includes a channel selector 810, a first force converter 820, a second force converter 830, and an estimator 840.

The channel selector 810 may select a channel of the pulse wave sensor 710 for estimating blood pressure based on the blood vessel position and the sensor position information, which are included in the structure information of the object.

For example, if the pulse wave sensor 710 has a single channel including a light source and a light receiver, the channel selector 810 may guide a user on a contact position of the object based on the blood vessel position and the sensor position information, which are included in the structure information of the object.

FIG. 9A is a diagram explaining an example of the pulse wave sensor 710 having a single channel 92. The channel selector 810 may display an image of a finger 90 through the output interface 760, and may display a blood vessel position 91 of the finger which is superimposed on a position of the channel 92 of the pulse wave sensor 710, so that a user may place the blood vessel position of the finger on the channel 92.

In another example, if the pulse wave sensor 710 has a plurality of channels for measuring a plurality of pulse wave signals at multiple points of the object, the channel selector 810 may determine a proper channel based on the blood vessel position of the object and the sensor position.

FIG. 9B is a diagram explaining an example of the pulse wave sensor 710 having multiple channels 93 for measuring a plurality of pulse wave signals at multiple points of the finger 90. Each of the channels ch1, ch2, and ch3 may include a light source and a light receiver. For example, upon receiving a request for estimating blood pressure, the channel selector 810 may select one of the multiple channels 93 by using the blood vessel position 91 of the finger 90 and the sensor position information, and may drive the selected channel. For example, the channel selector 810 may drive a channel ch3, which is located closest to the blood vessel position 91, among the channels ch1, ch2, and ch3 of the pulse wave sensor 710. Alternatively, the channel selector 810 may obtain pulse wave signals from each of the channels ch1, ch2, and ch3 by simultaneously or sequentially driving the multiple channels 93 of the pulse wave sensor 710, and may select the channel ch3, which is located closest to the blood vessel position 91, as a channel for estimating blood pressure.

FIG. 9C is a diagram explaining an example of the pulse wave sensor 710 having multiple channels 93 for measuring a plurality of pulse wave signals at the same time in a predetermined area of the finger 90. For example, the multiple channels 95 may include light sources, and a plurality of detector arrays or CMOS image sensors spaced apart from the light sources by a predetermined distance. The channel selector 810 may determine a channel ch, which is located closest to the blood vessel position 91, as a channel for estimating blood pressure among the multiple channels 95.

A first force converter 820 may convert a force, measured by the force sensor 720, into a first force at a pre-defined reference position based on a position of the channel of the pulse wave sensor 710, which is selected by the channel selector 810, and a reference point of the object. In this case, the reference point of the object may be the tip BP of a fingernail as illustrated in FIGS. 9A to 9C.

For example, the first force converter 820 may convert the measured force into a force, in which a sensor position is reflected, by applying a relationship equation such as the following Equations 2 and 3, which are examples.

$$fr(d) = \frac{f}{BP} = (a1 \times d) + a2 \quad \text{[Equation 2]}$$

Herein, f denotes an estimated oscillometric blood pressure value (e.g., estimated MAP) obtained based on the pulse wave signal at the sensor position; BP denotes a reference blood pressure (e.g., actual MAP); a1 and a2 denote coefficients defined by preprocessing; d denotes a distance between the reference point of the finger 90 and the sensor position as illustrated in FIGS. 9A to 9C; and fr(d) denotes a value for correcting the force measured by the force sensor 720 by reflecting the sensor position of the object.

$$BP = \frac{f}{fr(d_{mes})} = \frac{f'}{fr(d_{des})} \quad \text{[Equation 3]}$$

$$f' = f \times fr(d_{des}) / fr(d_{mes})$$

The above Equation 3 represents a relationship equation assuming that blood pressure BP at a measurement position of a user, i.e., the sensor position, is equal to blood pressure BP at a desired reference position. Here, $d_{mes}$ denotes a distance between the reference point of the user's finger and the sensor position; f denotes a contact force measured at the sensor position; fr($d_{mes}$) denotes a first correction value used for correcting the force at the sensor position using the above Equation 2; $d_{des}$ denotes a distance between the reference point of the user's finger and the reference position; fr($d_{des}$) denotes a second correction value corrected to the force at the reference position using the above Equation 2; and f' denotes a first force to be obtained at the reference position.

Once the first force converter 820 obtains the first force in which the sensor position is reflected, the second force converter 830 may convert the first force into a second force in which an anatomical structure of the object is reflected. As described above, the second force converter 830 may convert the first force into the second force, in which the structure of the object is reflected, by using the above Equation 1.

The estimator 840 may estimate blood pressure by using the force converted by the second force converter 830. As described above with reference to FIGS. 4A and 4B, the estimator 840 may estimate blood pressure using oscillometry.

FIG. 10 is a flowchart illustrating a method of estimating bio-information according to an embodiment of the present disclosure. The method of FIG. 10 is an example of a method of estimating bio-information which is performed by the aforementioned apparatuses 100a, 100b, and 500 for estimating bio-information. Various embodiments of estimating bio-information are described above in detail, and thus will be briefly described below.

Upon receiving a request for estimating bio-information from a user in operation 1010, the apparatus for estimating bio-information may check whether there is structure information of an object in operation 1020.

Then, upon checking, if there is no structure information of the object in a storage (operation 1020—NO), the apparatus for estimating bio-information may obtain structure information of the object in operation 1030. For example, as described above, the apparatus for estimating bio-information may directly receive input of structure information of the object from a user, or may obtain structure information of the object by analyzing an ultrasonic image, an MRI image, etc., which are acquired by an external device.

Subsequently, upon checking, if there is the structure information of the object (operation 1020—YES), the apparatus for estimating bio-information may obtain a pulse wave signal of the object through a pulse wave sensor in operation 1040, and may obtain force/pressure applied by the object to the pulse wave sensor in operation 1050.

Next, the apparatus for estimating bio-information may convert the force/pressure, obtained in operation 1050, based on the structure information of the object in operation 1060. For example, the apparatus for estimating bio-information may combine the structure information of the object, such as a ratio or difference between a blood vessel depth and a bone depth, and may convert the force by applying the combination result to the measured force.

Then, the apparatus for estimating bio-information may estimate bio-information in operation 1070 based on the pulse wave signal obtained in operation 1040 and the force converted in operation 1060.

Subsequently, the apparatus for estimating bio-information may output a bio-information estimation result in operation 1080. For example, the apparatus for estimating bio-information may provide a user with information, such as the estimated bio-information values, warning, measures, a bio-information estimation history, etc., in various manners by properly using a display, a speaker, a haptic device, and the like.

FIG. 11 is a flowchart illustrating a method of estimating bio-information according to another embodiment of the present disclosure. The method of FIG. 11 is an example of a method of estimating bio-information which is performed by the aforementioned apparatus 700 for estimating bio-information, which is described above in detail, and thus will be briefly described below.

Upon receiving a request for estimating bio-information from a user in operation 1111, the apparatus for estimating bio-information may obtain sensor position information when an object is in contact with a pulse wave sensor in operation 1112. In this case, the sensor position information may be obtained based on an image of the object, which is acquired by an external image capturing device, or a fingerprint image acquired by a fingerprint sensor.

Then, the apparatus for estimating bio-information may obtain a pulse wave signal of the object through the pulse wave sensor in operation 1113, and may obtain force/pressure applied by the object to the pulse wave sensor in operation 1114. In this case, if the pulse wave sensor has a single channel including one light source and one light receiver, the apparatus for estimating bio-information may guide a user to place a blood vessel position of the object on a position of the channel of the pulse wave sensor.

Subsequently, the apparatus for estimating bio-information may select a channel of the pulse wave sensor based on the sensor position information and the blood vessel position of the object in operation 1115. If the pulse wave sensor has multiple channels for obtaining pulse wave signals at multiple points of the object, the apparatus for estimating bio-information may select a channel which is located closest to the blood vessel position of the object.

Next, the apparatus for estimating bio-information may convert a force based on a position of the selected channel and a reference position of the object in operation 1116. For example, the apparatus for estimating bio-information may convert the force into a force, in which the sensor position is reflected, by using a pre-defined conversion equation based on a distance between the reference position of the object and the position of the selected channel.

Then, the apparatus for estimating bio-information may convert the force, in which the sensor position is reflected, into a force, in which structure characteristics of the object are reflected, by using structure information of the object in operation 1117. As described above, the apparatus for estimating bio-information may convert the force by applying, for example, a ratio or difference between a blood vessel depth or a bone depth, and the like.

Subsequently, the apparatus for estimating bio-information may estimate bio-information in operation 1118 based on the pulse wave signal obtained in operation 1113 and the force converted in operation 1117.

Next, the apparatus for estimating bio-information may output a bio-information estimation result in operation 1119.

Figure 12:
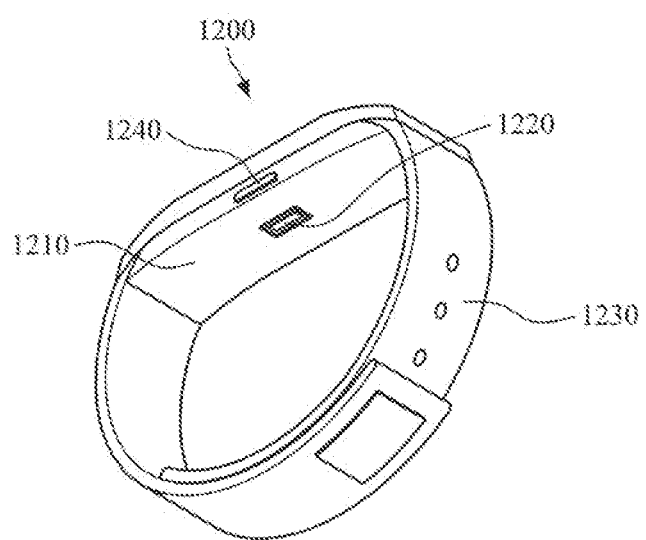
FIG. 12 is a diagram illustrating an example of a wearable device.

FIG. 12 is a diagram illustrating an example of a wearable device. Various embodiments of the aforementioned apparatuses 100a, 100b, 500, and 700 for estimating bio-information may be mounted in the wearable device.

Referring to FIG. 12, the wearable device 1200 includes a main body 1210 and a strap 1230.

The strap 1230, which is connected to both ends of the main body 1210, may be flexible so as to be bent around a user's wrist. The strap 1230 may be composed of a first strap and a second strap which are separated from each other. Respective ends of the first strap and the second strap are connected to the main body 1210, and the other ends thereof may be connected to each other via a connecting means. In this case, the connecting means may be formed as magnetic connection, Velcro connection, pin connection, and the like, but is not limited thereto. Further, the strap 630 is not limited thereto, and may be integrally formed as a non-detachable band.

In this case, air may be injected into the strap 1230, or the strap 1230 may be provided with an air bladder to have elasticity according to a change in pressure applied to the wrist, and may transmit the change in pressure of the wrist to the main body 1210.

A battery may be embedded in the main body 1210 or the strap 1230 to supply power to the wearable device 1200.

The main body 1210 may include a sensor part 1220 mounted on one side thereof. The sensor part 1220 may include a pulse wave sensor for measuring pulse wave signals. The pulse wave sensor may include a light source for emitting light onto skin of a wrist or a finger, a light receiver, such as a contact image sensor (CIS) optical sensor, a photodiode, etc., which detects light scattered or reflected from the wrist or the finger. The pulse wave sensor may have multiple channels for measuring pulse wave signals at multiple points of the wrist, the finger, etc., and each of the channels may include a light source and a light receiver, or may include a plurality of light sources for emitting light of different wavelengths. In addition, the sensor part 1220 may further include a force/pressure sensor for measuring force/pressure between the wrist or finger and the sensor part 1220. Furthermore, the sensor part 1220 may further include a fingerprint sensor, an ultrasonic sensor, and the like, which may be stacked on top of each other.

A processor may be mounted in the main body 1210. The processor may be electrically connected to modules mounted in the wearable device 1200. The processor may generate an oscillogram based on the pulse wave signals and the contact force/pressure, which are measured by the sensor part 1220, and may estimate blood pressure based on the obtained oscillogram. In this case, the processor may convert the force/pressure by using anatomical structure information of the finger, sensor position information, and the like, and may estimate blood pressure by using the converted force, thereby improving accuracy in estimating blood pressure.

Further, the main body 1210 may include a storage which stores reference information for estimating blood pressure and performing various functions of the wearable device 1200, and information processed by various modules thereof.

In addition, the main body 1210 may include a manipulator 1240 which is provided on one side surface of the main body 1210, and receives a user's control command and transmits the received control command to the processor. The manipulator 1240 may have a power button to input a command to turn on/off the wearable device 1200.

Further, a display for outputting information to a user may be mounted on a front surface of the main body 1210. The display may have a touch screen for receiving touch input. The display may receive a user's touch input and transmit the touch input to the processor, and may display processing results of the processor.

Moreover, the main body 1210 may include a communicator for communication with an external device. The communicator may transmit a blood pressure estimation result to the external device, e.g., a user's smartphone.

Figure 13:
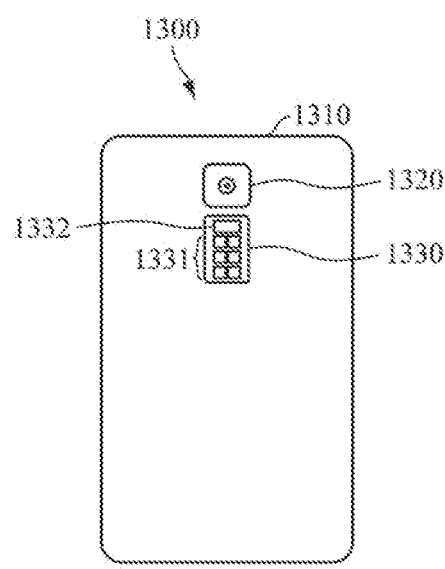
FIG. 13 is a diagram illustrating an example of a smart device.

FIG. 13 is a diagram illustrating an example of a smart device. In this case, the smart device may include a smartphone, a tablet PC, and the like. The smart device may include functions of the aforementioned apparatuses 100*a*, 100*b*, 500, and 700 for estimating bio-information.

Referring to FIG. 13, the smart device 1300 includes a main body 1310 and a pulse wave sensor 1330 mounted on one surface of the main body 1310. For example, the pulse wave sensor 1330 may include one or more light sources 1332 disposed at predetermined positions thereof. The one or more light sources 1332 may emit light of different wavelengths. In addition, in order to measure pulse wave signals at multiple points of the object, a plurality of light receivers 1331 may be disposed at positions spaced apart from the light sources 1332 by a predetermined distance. However, this is merely an example, and the pulse wave sensor 1330 may have various shapes as described above. Further, a force/pressure sensor for measuring a contact force/pressure of a finger may be mounted in the main body 1310 at a lower end of the pulse wave sensor 1330.

Moreover, a display may be mounted on a front surface of the main body 1310. The display may visually output a blood pressure estimation result, a health condition evaluation result, and the like. The display may include a touch screen, and may receive information input through the touch screen and transmit the information to a processor.

The main body 1310 may include an image sensor 1320 as illustrated in FIG. 13. The image sensor 1320 may capture various images, and may acquire, for example, an image of a finger being in contact with the pulse wave sensor 1330. In addition, when an image sensor based on the CIS technology is mounted in the light receivers 1331 of the pulse wave sensor 1330, the image sensor 1320 may be omitted.

As described above, the processor may convert the force, measured by the force sensor, based on the structure information of the object and/or the sensor position information obtained when the object is in contact with the pulse wave sensor, and may estimate blood pressure based on the converted force using oscillometry.

The present disclosure can be realized as a computer-readable code written on a non-transitory computer-readable recording medium. The non-transitory computer-readable recording medium may be any type of recording device in which data is stored in a computer-readable manner.

Examples of the non-transitory computer-readable recording medium include a ROM, a RAM, a CD-ROM, a magnetic tape, a floppy disc, an optical data storage, and a carrier wave (e.g., data transmission through the Internet). The non-transitory computer-readable recording medium can be distributed over a plurality of computer systems connected to a network so that a computer-readable code is written thereto and executed therefrom in a decentralized manner. Functional programs, code, and code segments needed for realizing the present disclosure can be readily deduced by programmers of ordinary skill in the art to which the disclosure pertains.

The present disclosure has been described herein with regard to example embodiments. However, it will be obvious to those skilled in the art that various changes and modifications can be made without changing technical conception and essential features of the present disclosure. Thus, it is clear that the above-described embodiments are illustrative in all aspects and are not intended to limit the present disclosure.

What is claimed is:

1. An apparatus for estimating bio-information, the apparatus comprising:
a pulse wave sensor configured to measure a pulse wave signal from an object;
a force sensor configured to measure a first force exerted between the object and the pulse wave sensor; and
a processor configured to:
convert the first force into a second force, based on structure information of the object; and
estimate the bio-information, based on the pulse wave signal and the second force,
wherein the structure information of the object comprises at least one of a blood vessel position, a blood vessel depth, and a bone depth, and
wherein the processor is further configured to convert the first force into the second force, based on at least one of a ratio between the blood vessel depth and the bone depth and a difference between the blood vessel depth and the bone depth.

2. The apparatus of claim 1, wherein the processor is further configured to obtain the structure information of the object based on a user input and at least one of an optical image, an ultrasonic image, a magnetic resonance imaging (MRI) image, and a photoacoustic image of the object.

3. The apparatus of claim 1, wherein the processor is further configured to obtain sensor position information indicative of a position of the pulse wave sensor with respect to the object, based on the object being in contact with the pulse wave sensor.

4. The apparatus of claim 3, wherein the processor is further configured to obtain the sensor position information by analyzing a relative position between the object and the pulse wave sensor, based on an image of the object being in contact with the pulse wave sensor.

5. The apparatus of claim 3, wherein the apparatus further comprises a fingerprint sensor, and wherein the processor is further configured to obtain the sensor position information, based on a fingerprint image obtained by the fingerprint sensor.

6. The apparatus of claim 3, wherein the processor is further configured to convert the first force into a third force, based on the sensor position information, and convert the third force into the second force in which the structure information of the object is reflected.

7. The apparatus of claim 6, wherein the processor is further configured to convert the first force into the third force, based on a distance between a predetermined reference point of the object and the position of the pulse wave sensor.

8. The apparatus of claim 7, wherein by using a predefined function, the processor is further configured to:
obtain a first correction value, based on the distance between the predetermined reference point and the position of the pulse wave sensor;
obtain a second correction value, based on a distance between the predetermined reference point and a reference position; and
convert the first force into the third force, based on the first correction value and the second correction value.

9. The apparatus of claim 3, wherein the pulse wave sensor has a plurality of channels for measuring pulse wave signals at a plurality of points of the object, and wherein the processor is further configured to:
select at least one of the plurality of channels, based on the blood vessel position of the object and the sensor position information; and
convert the first force into a third force, based on a distance between a predetermined reference point of the object and the selected at least one of the plurality of channels.

10. The apparatus of claim 9, wherein the processor is further configured to select the at least one of the plurality of channels, which is located closest to the blood vessel position of the object, based on the sensor position information.

11. The apparatus of claim 1, wherein the apparatus further comprises an area sensor configured to measure a contact area between the object and the pulse wave sensor, based on the object being in contact with the pulse wave sensor and changing a force applied to the pulse wave sensor.

12. The apparatus of claim 11, wherein the processor is further configured to:
obtain a contact pressure, based on the second force and the measured contact area; and
estimate the bio-information, based on the contact pressure and the pulse wave signal.

13. The apparatus of claim 1, wherein the bio-information comprises one or more of blood pressure, vascular age, arterial stiffness, aortic pressure waveform, vascular compliance, stress index, fatigue level, skin age, and skin elasticity.

14. A method of estimating bio-information, the method comprising:
measuring a pulse wave signal from an object;
measuring a first force exerted between the object and a pulse wave sensor;
converting the first force into a second force, based on structure information of the object; and
estimating the bio-information based on the pulse wave signal and the second force,
wherein the structure information of the object comprises at least one of a blood vessel position, a blood vessel depth, and a bone depth, and
wherein the converting of the first force comprises converting the first force, based on at least one of a ratio between the blood vessel depth and the bone depth and a difference between the blood vessel depth and the bone depth.

15. The method of claim 14, further comprising:
in response to receiving a request for estimating the bio-information from a user, determining whether the structure information of the object of the user exists; and
in response to determining that the structure information of the object does not exist, obtaining the structure information of the object.

16. The method of claim 14, further comprising obtaining sensor position information indicative of a position of the pulse wave sensor with respect to the object when the object is in contact with the pulse wave sensor.

17. The method of claim 16, wherein the converting of the first force into the second force comprises:
converting the first force into a third force, based on the sensor position information; and
converting the third force into the second force, based on the structure information of the object.

18. The method of claim 17, wherein the converting of the first force into the third force comprises converting the first force into the third force, based on a distance between a predetermined reference point of the object and the position of the pulse wave sensor.

19. The method of claim 18, wherein the converting of the first force into the third force comprises:
- by using a pre-defined function, obtaining a first correction value based on the distance between the predetermined reference point and the position of the pulse wave sensor;
- obtaining a second correction value based on a distance between the predetermined reference point and a reference position; and
- converting the first force into the third force, based on the first correction value and the second correction value.

20. The method of claim 17, wherein the converting of the first force into the third force comprises:
- in response to the pulse wave sensor having a plurality of channels for measuring pulse wave signals at a plurality of points of the object, selecting at least one of the plurality of channels based on blood vessel position information of the object and the sensor position information; and
- converting the first force into the third force, based on a distance between a predetermined reference point of the object and the at least one of the plurality of channels.

21. The method of claim 14, further comprising:
- measuring a contact area, based on the object being in contact with the pulse wave sensor and changing a force applied to the pulse wave sensor.

22. The method of claim 21, wherein the estimating of the bio-information comprises:
- obtaining a contact pressure, based on the second force and the contact area; and
- estimating the bio-information, based on the contact pressure and the pulse wave signal.

23. An electronic device for estimating bio-information of a user, the electronic device comprising a processor configured to:
- obtain, from a pulse wave sensor of the electronic device, a pulse wave signal of the user;
- obtain a first force value corresponding to a force exerted between an object of the user and the pulse wave sensor of the electronic device;
- obtain sensor position information indicative of a position of the pulse wave sensor with respect to the object of the user;
- obtain blood vessel position information indicative of a position of a blood vessel of the object of the user, the blood vessel position information comprising a blood vessel depth;
- identify a second force value, based on the first force value, the sensor position information, and the blood vessel position information; and
- estimate the bio-information, based on the pulse wave signal and the second force value,
- wherein the second force value is identified based on at least one of a ratio between the blood vessel depth and a bone depth and a difference between the blood vessel depth and qathe bone depth.

24. The electronic device of claim 23, wherein the processor is further configured to:
- obtain bone position information indicative of a position of a bone of the object; and
- identify the second force value, based on the bone position information.

* * * * *